United States Patent [19]
Vrba et al.

[11] Patent Number: 6,120,522
[45] Date of Patent: Sep. 19, 2000

[54] SELF-EXPANDING STENT DELIVERY CATHETER

[75] Inventors: Anthony C. Vrba; Joel R. Munsinger, both of Maple Grove; Jon St. Germain, Elk River, all of Minn.

[73] Assignee: Scimed Life Systems, Inc., Maple Grove, Minn.

[21] Appl. No.: 09/141,209

[22] Filed: Aug. 27, 1998

[51] Int. Cl.⁷ ................................................ A61B 17/00
[52] U.S. Cl. ........................... 606/190; 623/1.11; 623/12
[58] Field of Search ............................ 606/1, 108, 192, 606/194, 198, 200; 623/1, 12, 1.11

[56] References Cited

U.S. PATENT DOCUMENTS

| | | |
|---|---|---|
| 4,732,152 | 3/1988 | Wallsten et al. . |
| 4,848,343 | 7/1989 | Wallsten et al. . |
| 4,875,480 | 10/1989 | Imbert . |
| 5,026,377 | 6/1991 | Burton et al. . |
| 5,108,416 | 4/1992 | Ryan et al. . |
| 5,201,757 | 4/1993 | Heyn et al. . |
| 5,484,444 | 1/1996 | Braunschweiler et al. . |
| 5,534,007 | 7/1996 | Germain et al. . |
| 5,702,364 | 12/1997 | Euteneuer et al. . |
| 5,772,669 | 6/1998 | Vrba . |
| 5,807,327 | 9/1998 | Green et al. . |
| 5,824,041 | 10/1998 | Lenker et al. . |
| 5,836,965 | 11/1998 | Jendersee et al. . |

FOREIGN PATENT DOCUMENTS

| | | |
|---|---|---|
| 0 408 245 A1 | 1/1991 | European Pat. Off. . |
| 0 554 579 A1 | 8/1993 | European Pat. Off. . |
| 0 657 142 A2 | 6/1995 | European Pat. Off. . |
| 0 696 447 A2 | 2/1996 | European Pat. Off. . |
| 0 819 411 A2 | 1/1998 | European Pat. Off. . |
| 96/36298 | 11/1996 | WIPO . |
| 97/09932 | 3/1997 | WIPO . |

Primary Examiner—Michael Buiz
Assistant Examiner—William Lewis
Attorney, Agent, or Firm—Vidas, Arrett & Steinkraus, P.A.

[57] ABSTRACT

The present invention provides a self-expanding stent delivery system comprising a catheter, a self-expanding stent having a plurality of interconnected expansion cells therein and concentrically arranged around the catheter near the distal end of the catheter, a retractable sheath for covering the stent constructed and arranged for retraction to release the stent to self-expand, and a stent holder abutting the stent for holding the stent in place until the retractable sheath is fully retracted. During retraction of the retractable cover, the stent holder prevents the stent from substantially moving longitudinally until the retractable sheath has been completely removed from the stent.

19 Claims, 7 Drawing Sheets

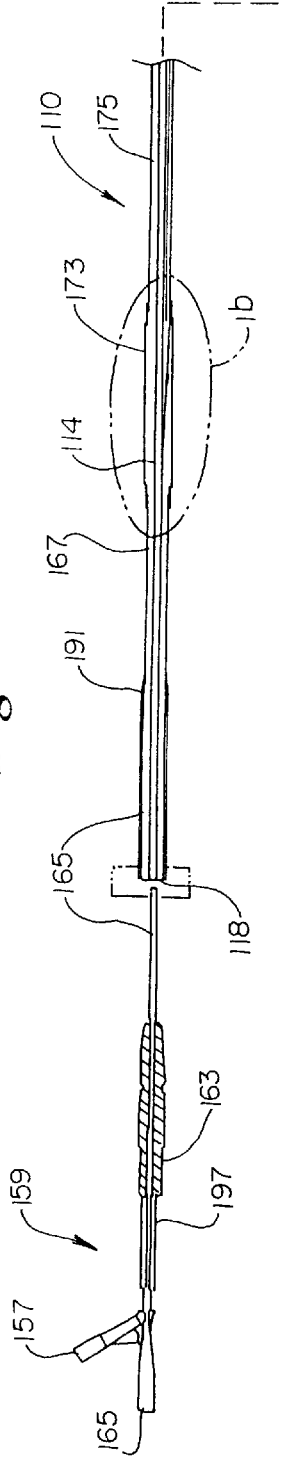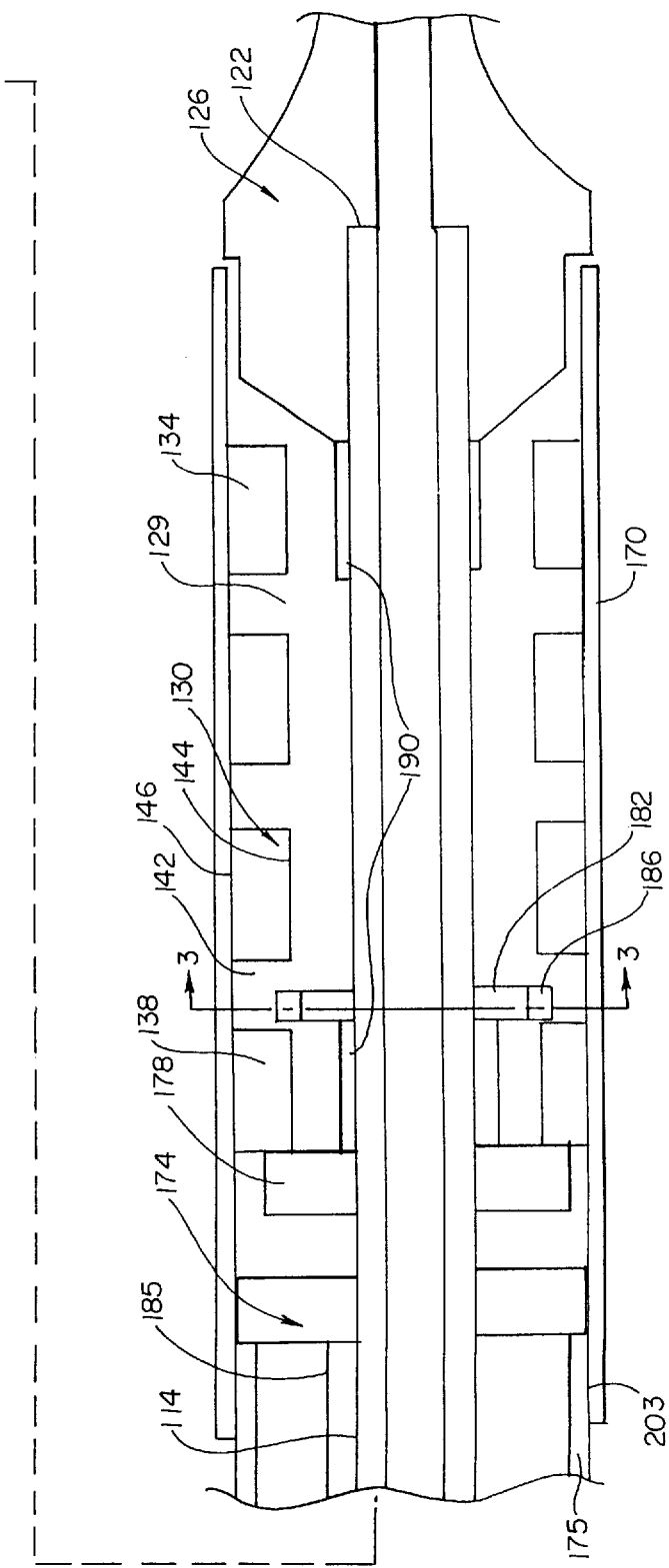
Fig. 1a

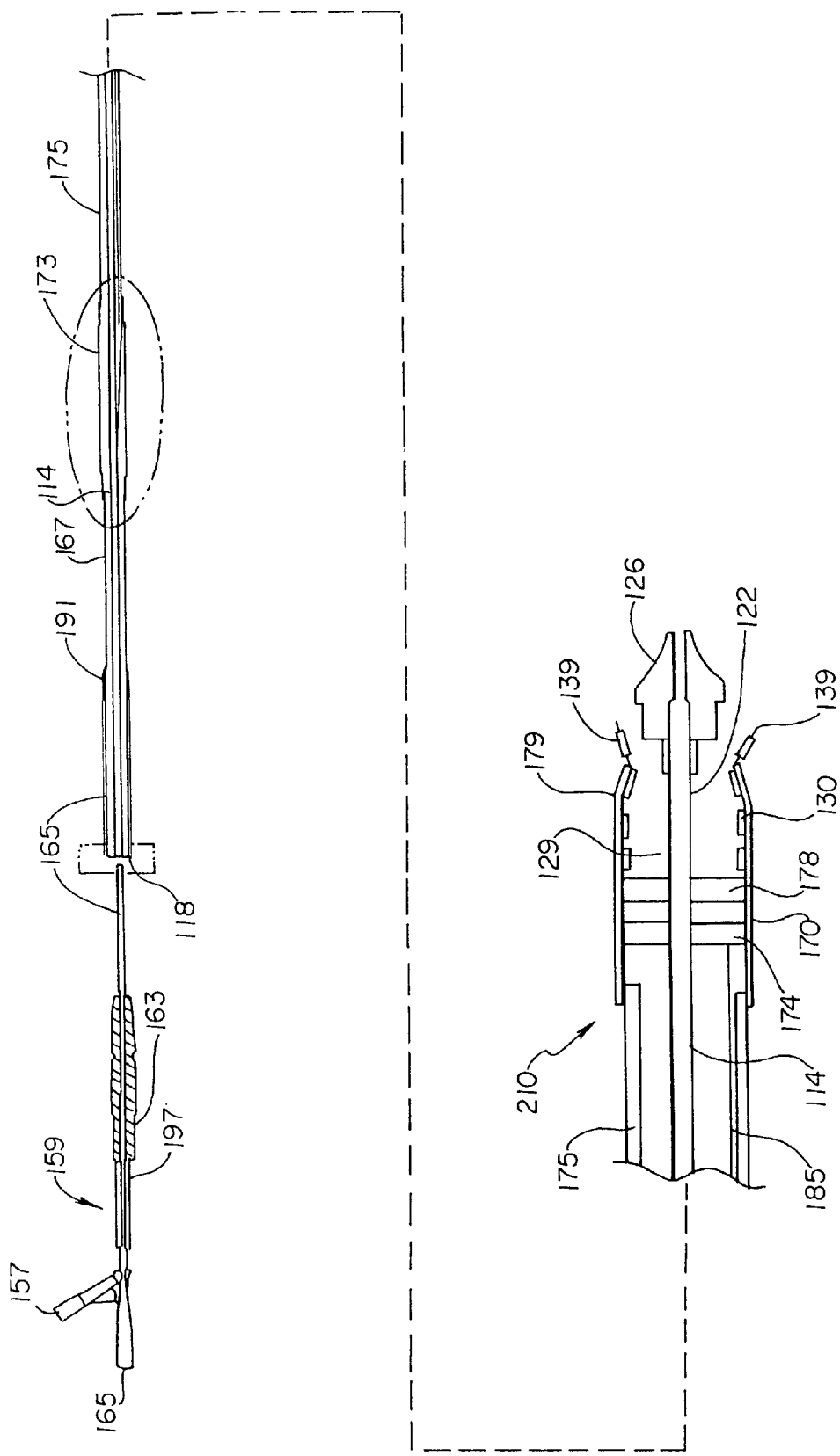

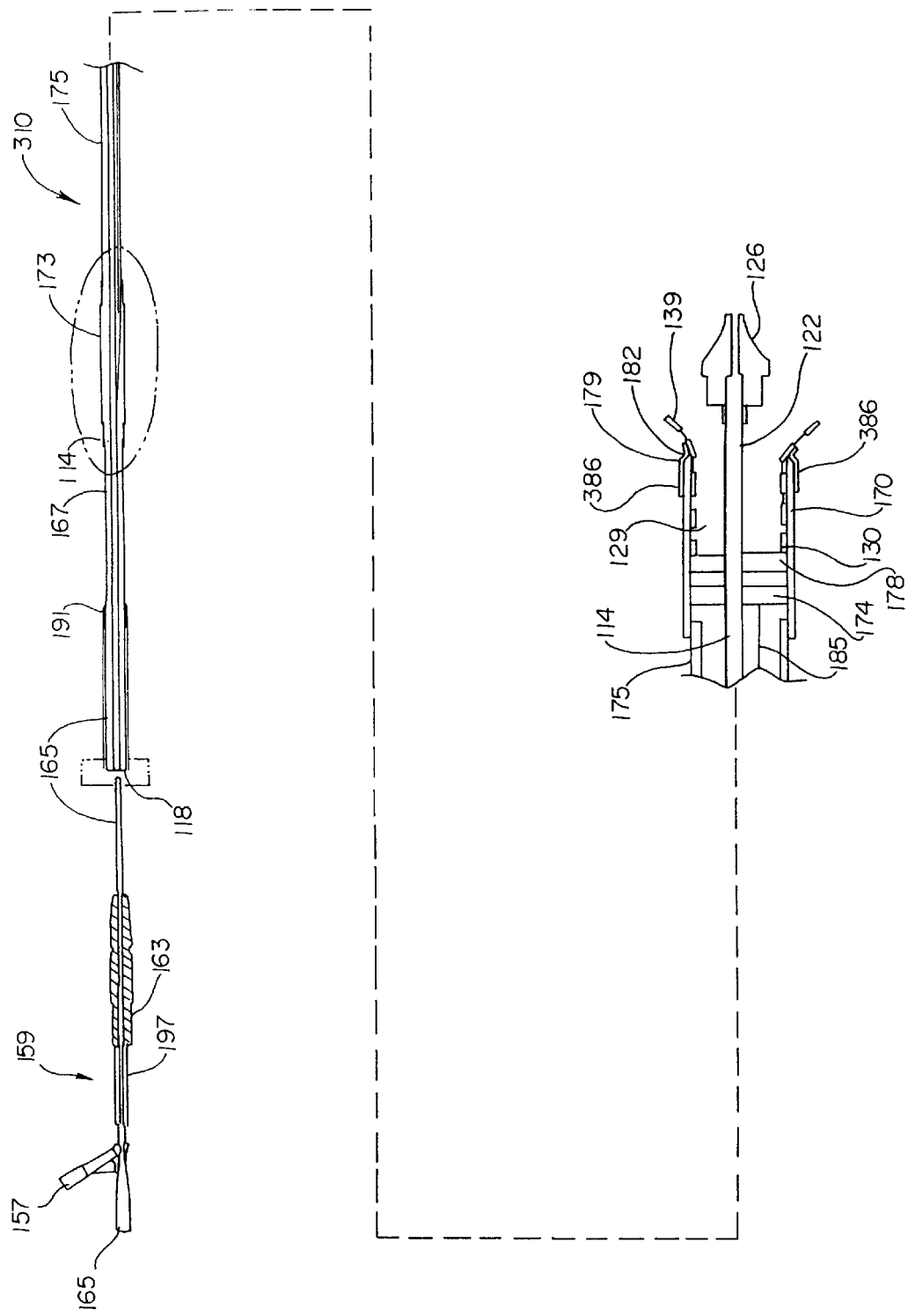

SELF-EXPANDING STENT DELIVERY CATHETER

BACKGROUND OF THE INVENTION

This invention relates to an assembly and method for delivering and deploying a self-expanding stent, particularly within a lumen of a body vessel. More specifically, this invention relates to the provision of a stent holder to maintain the stent on the catheter assembly during delivery to a stent deployment site and to prevent longitudinal movement of the stent prior to the stent fully expanding.

Stents and stent delivery assemblies are utilized in a number of medical procedures and situations, and as such their structure and function are well known. A stent is a generally cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Both self-expanding and inflation expandable stents are well known and widely available in a variety of designs and configurations. Self-expanding stents must be maintained under positive external pressure in order to maintain their reduced diameter configuration during delivery of the stent to its deployment site. Such pressure may be provided by a sheath overlying the stent.

In using such stents, it is often necessary to position the stent in a precise location within a bodily lumen. Because self-expanding stents have a tendency to move longitudinally before they are fully expanded, accurately positioning the stent in a desired location can prove difficult.

It is a goal of the present invention to provide a self-expanding stent delivery system with improved stent deployment accuracy which prevents longitudinal lurching of the stent during deployment and thereby facilitate the positioning of stents with greater precision. In particular, it is a goal of the present invention to provide a self-expanding stent delivery system having a stent holder which during retraction of the retractable sheath, prevents the stent from substantially moving longitudinally until the retractable sheath has been removed from the stent.

SUMMARY OF THE INVENTION

The present invention provides a self-expanding stent delivery system comprising a catheter having proximal and distal ends and a self-expanding stent, having proximal and distal ends, concentrically arranged around the catheter near the distal end of the catheter. The stent is characterized by an unexpanded state and, following expansion, by an expanded state. The stent delivery system also comprises a retractable sheath for covering the stent. The retractable sheath is constructed and arranged for retraction to release the stent to self-expand, and is located at the distal end of the catheter and mounted coaxially about the catheter. The stent delivery system further comprises a stent holder adjacent to at least a portion of the stent. The stent holder is constructed and arranged for holding the stent in place and preventing substantial longitudinal movement of the stent until the retractable sheath is retracted.

In one embodiment, the stent holder is constructed and arranged such that a portion of the stent holder extends into one or more retention openings in a stent.

In another embodiment, the stent holder is a profiled extrusion between the proximal end of the stent and the catheter, frictionally engaging the proximal end of the stent in the unexpanded state.

In another embodiment, the stent holder is located at the distal end of the retractable sheath and comprises a portion of the retractable sheath tapered inward toward the catheter and adjacent to the stent. The stent holder frictionally engages at least a portion of the stent as the retractable sheath is retracted and prevents the stent from moving substantially longitudinally.

In yet another embodiment, the stent holder comprises an elastic membrane situated at the distal end of the retractable sheath and adjacent to the stent. The stent holder is arranged so as to frictionally engage at least a portion of the stent during retraction of the sheath and prevent the stent from self deploying.

The present invention is directed more generally to a medical device delivery system comprising a catheter having proximal and distal ends. At the distal end of the catheter is a medical device mounting region. The delivery system includes a retractable sheath for covering the medical device mounting region. The retractable sheath, located at the distal end of the catheter and disposed coaxially about the catheter, is constructed and arranged for retraction from over the medical device mounting region. A medical device holder is adjacent to at least a portion of the medical device mountain region for holding a medical device in place until the retractable sheath is retracted. During retraction of the retractable sheath, the medical device holder prevents a medical device mounted on the medical device mounting region from substantially moving longitudinally until the retractable sheath has been removed from over a said medical device.

The present invention is also directed to a method of securing a stent to a stent delivery system. The method comprises the steps of providing a stent delivery system comprising a catheter with a stent mounting region thereon and a stent holder extending outward from the catheter in the stent mounting region and mounting a stent having one or more retention openings therein on the stent mounting region of the catheter, the stent holder extending into at least one of the retention openings so as to engage the stent.

The present invention is also directed to a method of securing a stent to a stent delivery system comprising the steps of providing a stent delivery system comprising a catheter with a stent mounting region thereon, the stent mounting region exposed. The system further comprises a retractable sheath having a stent holder extending from the distal end thereof, the retractable sheath retractable between a closed position in which the retractable sheath overlies the stent mounting region of the catheter and an open position in which the retractable sheath does not overly the mounting region. A stent is then mounted on the stent mounting region of the catheter and the retractable sheath moved so that it is in its closed position overlying the stent and stent mounting region of the catheter, the stent holder adjacent to the distal end of the stent and optionally engaging the stent.

The present invention is also directed to a method of controllably delivering a self expanding stent comprising the steps of mounting the stent in the unexpanded state on the catheter, surrounding at least a portion of the stent with a retractable sheath for preventing the stent from self expanding, engaging the stent with the stent holder to prevent the stent from substantially moving in a longitudinal direction, optionally purging the stent delivery system of air, inserting at least a portion of the stent delivery system into a bodily vessel, delivering the stent to a desired location in the body, fully retracting the retractable sheath thereby allowing the stent to self expand and withdrawing the stent delivery system.

BRIEF DESCRIPTION OF THE FIGURES

FIG. 1a shows a schematic side view of an inventive stent delivery system according to the invention.

FIG. 1b shows a partial exploded view of circled region 1b of FIG. 1a.

FIG. 6 shows a schematic side view of an inventive stent delivery system with a tapered retractable cover.

FIG. 7 shows a schematic side view of an inventive stent delivery system with retractable sheath having an elastic member.

DETAILED DESCRIPTION OF THE INVENTION

Figure 2B:
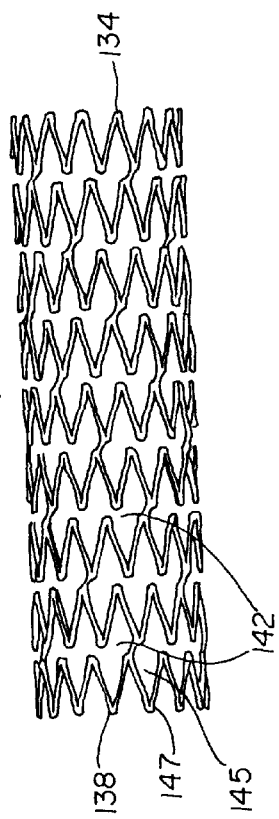
FIG. 2b shows a self-expanding stent in the expanded state for use with the inventive stent delivery system.

While this invention may be embodied in many different forms, there are described in detail herein specific preferred embodiments of the invention. This description is an exemplification of the principles of the invention and is not intended to limit the invention to the particular embodiments illustrated.

The present invention provides a self-expanding stent delivery system with a stent holder which prevents the stent from deploying before it is fully expanded. The self-expanding stents used with the inventive stent delivery system may be formed of any suitable bio-compatible material, although in a preferred embodiment, a self-expanding nitinol stent is used.

Turning to the Figures, FIG. 1a, a schematic of an embodiment of the inventive self-expanding stent delivery system, shown generally at 110, includes a catheter 114, preferably made of a polyimide braid, having a proximal end 118 and a distal end 122. Catheter 114 may house a guide wire (not shown) within and which extends within. Attached to distal end 122 of catheter 114 is a tip 126 preferably made of polyethylene. Distal tip 126 may be affixed to the catheter by an adhesive such as a urethane, an epoxy or the like.

Also at distal end 122 of catheter 114 is a self-expanding stent 130 (shown in the unexpanded state in FIGS. 1 and 2a) mounted thereon. Stent 130, as shown in the unexpanded state in FIG. 2a and in the expanded state in FIG. 2b, has a distal end 134 and a proximal end 138 and has a plurality of retention openings 142 therein. Retention openings 142 extend from inner surface 144 to outer surface 146 of the stent, as shown in FIG. 1a.

Stent 130 is covered by retractable sheath 170 which may be retracted by pulling on pull collar 174 attached thereto using pull wire 185 connected to pull collar 174 and extending to the proximal end of the stent delivery system 110. Pull collar 174 may be a ring-shaped member made of stainless steel or preferably of a radio-opaque material such as gold affixed to the interior of sheath 170 by an appropriate adhesive such as an epoxy, a urethane or a cyanoacrylate. The retractable sheath is preferably formed of a material which provides tensile strength, but is flexible, such as polyethylene. Retractable sheath 170 abuts tip 126 to form stent chamber 129.

Proximal to stent 130 is a bumper 178. Bumper 178 may be made of polyethylene and is affixed to catheter 114 by an adhesive such as a urethane.

Stent 130 is held in place by stent holder 182 which extends outward from catheter 114. At least a portion 186 of stent holder 182 extends into one or more retention openings 142 at proximal end 138 of stent 130, as shown in FIG. 1. Finally, inventive stent delivery system 110 comprises one or more optional marker bands 190. As shown in FIG. 1a, marker bands 190 are located at the proximal and distal ends of the stent 130. Of course, marker bands 190 may be otherwise positioned or need not be used at all. Marker bands 190 are included to aid in positioning and may be affixed to catheter 114 by an adhesive such as a cyanoacrylate.

Figure 1B:
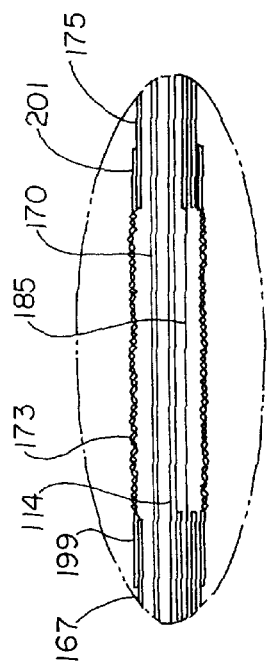

A wide variety of designs may be employed for the stent delivery system proximal to retractable sheath 170. In a preferred embodiment, as shown in FIG. 1a, stent delivery system proximal to sheath 170 comprises a proximal outer shaft, 165, preferably made of PEEK (polyetheretherketone) although a polyimide braid may also be used, and a distal outer shaft 167, preferably made of polyethylene, connected to the proximal outer shaft 165 at an adhesive point 191, preferably by means of a urethane adhesive. The distal outer shaft 167 is similarly connected at a second adhesive point 199 (preferably using a urethane adhesive) to a collapsible sheath/shaft 173. The collapsible sheath/shaft is collapsible in the longitudinal direction in an accordion manner and is most preferably made of HDPE (high density polyethylene), best shown in FIG. 1b. The collapsible shaft 173 is, in turn, connected to a proximal sheath, or spacer sheath, 175, which is preferably made of polyethylene, at a third adhesive point 201 (preferably using a urethane adhesive). The distal end of the proximal sheath 175 is adhered at point 203 (preferably using a urethane adhesive) to the proximal end of retractable sheath 170, which is preferably made of polyethylene.

Finally, the stent delivery system 110 includes a hand manifold, generally designated 159, which comprises a sheath actuator (sliding member) 163, a safety lock 197, which secures the sheath actuator 163 in place and is preferably made of polyethylene, a guide wire inlet 165 for controlling the guide wire from the proximal end, and a hydrating luer 157, for flushing.

The manifold and the stent delivery system in general, proximal to the retractable sheath, is further described in U.S. Pat. No. 5,534,007 to St. Germain and Olson and in WO 96/36298, both of which are incorporated herein in their entirety by reference.

Figure 3A:
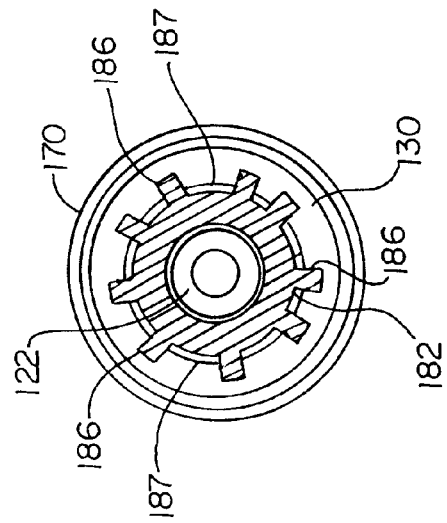
FIG. 3a is a cross sectional view of the inventive stent delivery system of FIG. 1 shown along view 3—3.
Figure 3B:
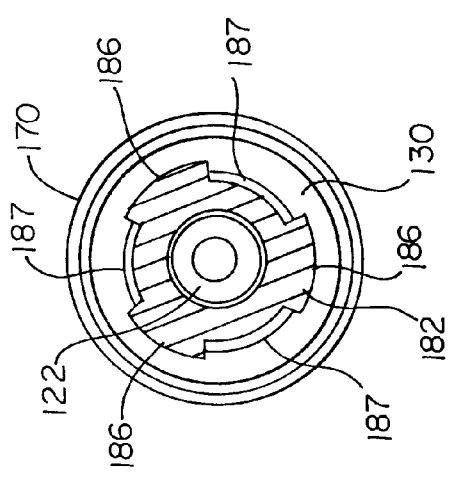
FIG. 3b is a cross sectional view of the inventive stent delivery system of FIG. 1 shown along view 3—3 where the stent holder has nine portions which extend into the retention openings of a stent.

In a preferred embodiment, as shown in FIG. 3a, stent holder 182 has three portions 186 which may extend into retention openings of a stent in the unexpanded state. Stent holder 182 may, of course, have fewer or additional portions 186 which may extend into retention openings. In another preferred embodiment, as shown in FIG. 3b, stent holder 182 has nine portions 186 which may extend into retention openings 142 of a stent in the unexpanded state. It is not necessary that the entire stent holder be situated underneath the proximal end of the stent, but at least a portion of the stent holder should be so situated. Although the invention is directed to embodiments in which the stent holder extends into one or more of the retention openings of the stent in the unexpanded state, it is desirable that the stent holder not extend into the retention openings of the stent in the expanded state. It is more desirable that the stent holder not extend beyond the outer surface of the stent in the unexpanded state. Of course, the width of the portions 186 which are intended to extend into the retention openings in the stent must be sized appropriately so as to fit into the openings.

It is also desirable that there be a gap, in or more places, between the stent holder and the stent so as to allow a fluid to be flushed through the stent bearing region of the stent delivery system through an optional flush lumen (not shown). As shown in FIGS. 3a and 3b, gaps 187 between stent holder 186 and stent 130 serve such a purpose.

Where the stent has a plurality of retention openings therein, it is desirable that the stent holder extend into one or more of the proximal most retention openings in the stent. More desirably, the stent holder should be disposed such that it engages the proximal-most portion 147 of the proximal-most retention opening 145 of the stent, as seen with clarity in FIG. 2b.

Figure 5:
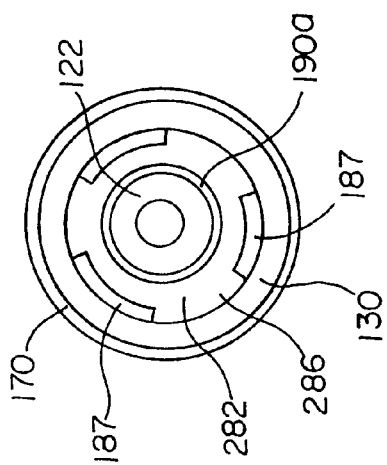
FIG. 5 shows a cross sectional view of the inventive stent delivery system of FIG. 4 shown along view 5—5.

It is also desirable that there be a gap, in one or more places, between the stent holder and the stent so as to allow a fluid to be flushed through the stent bearing region of the stent delivery system through an optional flush lumen (not shown). As shown in FIG. 5, gaps 187 between stent holder 282 and stent 130 serve such a purpose.

Figure 2A:
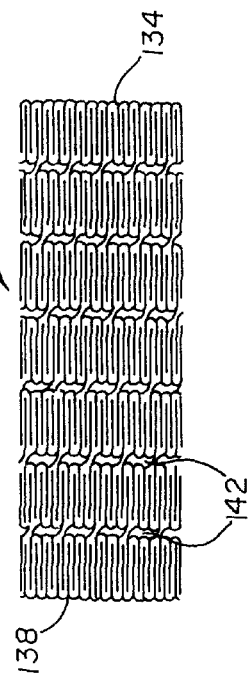
FIG. 2a shows a self-expanding stent in the unexpanded state for use with the inventive stent delivery system.

Although the stent shown in FIGS. 2a and 2b is a preferred stent for use with the above-described embodiment of the inventive stent delivery system, the invention may be used with a variety of stent designs that have retention openings therein. The invention is further intended for use with other medical treatment devices such as a vena cava filter having a retention opening therein and a graft, preferably self expanding, having an retention opening therein. The invention is also intended for use with other self-expanding medical treatment devices with and without retention openings therein.

While the stent holder may be made of a wide range of materials such as polyurethane or polyethylene, the stent holder should be sufficiently rigid to withstand any forces exerted on it by the stent in the unexpanded state. Specifically, the stent holder must be sufficiently rigid so as not to bend and release the stent as the stent exerts longitudinal forces on the stent holder. In one embodiment, the stent holder is a profiled ring attached to the distal end of the catheter and situated underneath the proximal end of the stent.

Figure 4:
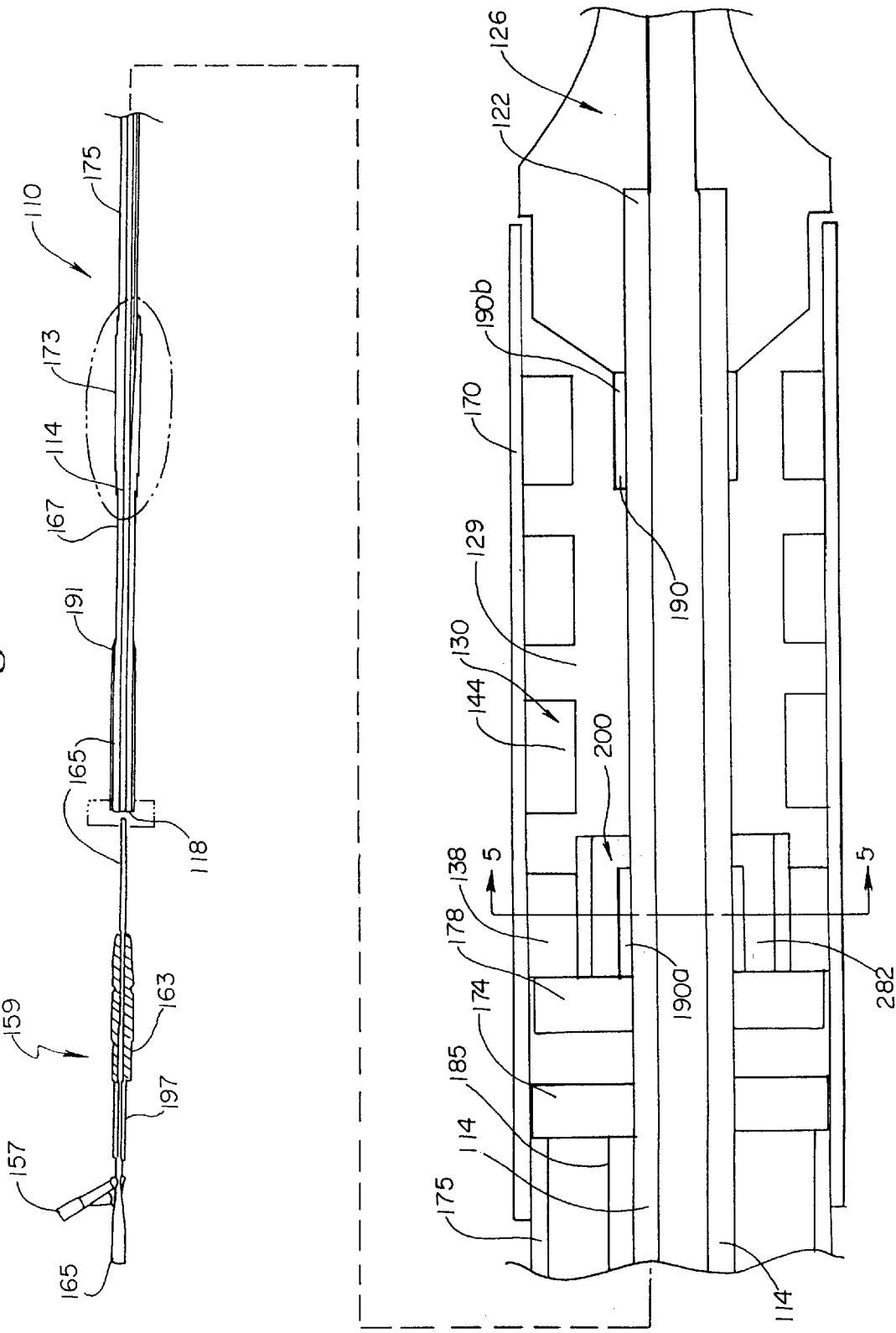
FIG. 4 shows a schematic side view of an inventive stent delivery system.

In another embodiment, an inventive self-expanding stent delivery system, shown generally in FIG. 4 at 110, includes a catheter 114. Catheter 114 has a proximal end 118 and a distal end 122. Distal end 122 of catheter 114 includes a tip 126, and further has a self-expanding stent 130 (shown in the unexpanded state in FIG. 2a and in the expanded state in FIG. 2b) mounted thereon. Stent 130 is covered by retractable sheath 170 which may be retracted by pulling on pull collar 174 attached thereto. Retractable sheath 170 abuts tip 126 to form stent chamber 129. Proximal to stent 130 is a bumper 178. Stent 130, as shown in FIGS. 4 and 5, is held in place by stent holder 282 which is compressed between the proximal end 138 of stent 130 and catheter 114 and thereby frictionally engages stent 130 preventing it from moving in a longitudinal direction until stent 130 is fully expanded so as to no longer engage stent holder 282. Finally, inventive stent delivery system 110 comprises one or more optional marker bands 190. As shown in FIG. 4, two optional marker bands are used including a proximal marker band 190a and a distal marker band 190b. As shown in FIGS. 4 and 5, proximal marker band 190a is situated between stent holder 282 and catheter 114. The portion 200 of stent holder 282 which extends beyond proximal marker band 190a extends from catheter 114. Of course, the use of the marker bands is optional as is their location underneath the stent.

It is also desirable that there be a gap, in one or more places, between the stent holder and the stent so as to allow a fluid to be flushed through the stent bearing region of the stent delivery system through an optional flush lumen (not shown). As shown in FIG. 5, gaps 187 between stent holder 282 and stent 130 serve such a purpose.

While stent holder 282 may be made of any suitable material, in a preferred embodiment, stent holder 282 is a profiled extrusion. Of course, the portion of stent holder 282 must not be such as to mar or scratch stent 30. Suitable materials include polyethylene, polyurethane, polystyrene and polyesters.

Although the embodiment shown in FIG. 4 is shown with a stent having retention openings therein, the presence of retention openings in the stent is not necessary to the successful operation of the embodiment shown in FIG. 4. As such, the embodiment is not intended to be limited to use with the stent shown in FIG. 2a and FIG. 2b, but rather may be used with a wide array of self-expanding stents.

The remainder of the stent delivery system proximal to retractable sheath 170 has been described above, in reference to FIGS. 1–3 and will not be repeated here.

Although the embodiments of FIG. 1 and FIG. 4 appear similar in that both stent holders are profiled, they differ in that the stent holder shown in FIG. 1 protrudes into retention openings of the stent whereas the stent holder of FIG. 4 frictionally engages the inner surface of the stent and does not protrude into the stent. As such, the dimensions of the protruding portions 186 and 286 of the stent holders may differ.

In another embodiment, an inventive self-expanding stent delivery system, shown generally in FIG. 6 at 210, includes a catheter 114 having a proximal end 118 and a distal end 122. Distal end 122 of catheter 114 includes a tip 126, and further has a self-expanding stent 130 (shown in the unexpanded state in FIG. 2) mounted thereon. Stent 130 is covered by retractable sheath 170 which may be retracted by pulling on pull collar 174 attached thereto via pull wire 185 extending from pull collar 174 to the manifold 159. Although the delivery system is shown with the retractable sheath partially retracted, when retractable sheath 170 is closed it abuts tip 126 to form stent chamber 129. Proximal to stent 130 is a bumper 178. Distal end 179 of retractable sheath 170, integral with retractable sheath 170, is tapered inward thereby forming a stent holder. The stent holder (distal end 179) is adjacent to the stent prior to retraction of the sheath. During retraction of the sheath, the stent holder engages the stent, resulting in an increased frictional force between stent 130 and distal end 179 and preventing stent 130 from moving longitudinally along the catheter in a distal direction until retractable sheath 170 has been fully retracted from stent 130. Finally, inventive stent delivery system 210 comprises one or more optional marker bands (not shown).

Inwardly tapered portion 179 of the retractable sheath 170 is preferably made of a material, such as polyethylene, that will not scratch or otherwise mar stent 130 as portion 179 passes over stent 130.

FIG. 6 further depicts a portion 139 of stent 130 after inwardly tapered portion 179 has passed over it and portion 139 of stent 130 begins to expand.

The remainder of the stent delivery system proximal to retractable sheath 170 has been described above, in reference to FIGS. 1–3 and will not be repeated here.

In another embodiment, an inventive self-expanding stent delivery system, shown generally in FIG. 7 at 310, includes a catheter 114 having a proximal end 118 and a distal end 122. Distal end 122 of catheter 114 includes a tip 126, and further has a self-expanding stent 130 (shown in the unexpanded state in FIG. 2) mounted thereon. Stent 130 is covered by retractable sheath 170 which may be retracted by pulling on pull collar 174 attached thereto via pull wire 185 extending from pull collar 174 to the manifold 159. Although the delivery system is shown with the retractable sheath partially retracted, when retractable sheath 170 is closed it abuts tip 126 to form stent chamber 129. Proximal to stent 130 is a bumper 178. Distal end 179 of retractable sheath 170 has a stent holder consisting of an elastic membrane 386 bonded to distal end of retractable sheath 170. Elastic membrane 386, which may be tapered inward, exerts an increased frictional force on stent 130 during retraction of the sheath thereby preventing stent 130 from moving longitudinally in a distal direction until retractable sheath 170 has been fully retracted from stent 130. Finally, inventive stent delivery system 310 comprises one or more optional marker bands (not shown).

FIG. 7 further depicts a portion 139 of stent 130 after inwardly tapered portion 182 has passed over it and portion 139 of stent 130 begins to expand.

As in the previously described embodiment, elastic membrane 386, with its inwardly tapered element 182 is preferably constructed of a suitable material which will not mar or scratch stent 130 as it contacts the stent.

Elastic membrane 386 may be made of any suitable material such as polyolefin copolymers and may be fixedly attached to retractable sheath 170 and to inwardly tapered element 182 adhesively or through any other suitable method.

Although the pull collars described herein may be made of stainless steel or other suitable materials, it is preferred that they be made of a radiopaque material such as gold.

While the portion of the stent delivery system proximal to the retractable sheath disclosed above is further described in U.S. Pat. No. 5,534,007, other designs may be used as well for that portion including the other embodiments disclosed in U.S. Pat. No. 5,534,007. Similarly, the proximal end of retractable sheath 170 may include a sliding seal to allow the retractable sheath 170 to slide proximally along catheter 114. Additionally, a midshaft seal may also be present. Such a system is described in copending commonly assigned applications 08/722,834 filed Sep. 27, 1996, now U.S. Pat. No. 5,772,665 and continuation-in-part application 09/071,484 filed May 1, 1998, now U.S. Pat. No. 5,957,920. The entire contents of both applications are hereby incorporated in their entirety by reference.

While the above-described stent delivery systems all comprise pull collars for retracting the retractable cover, other suitable pull back means may also be used. Other suitable pull back systems include hydraulic or screw arrangements such as described in U.S. Pat. No. 4,732,152 to Wallsten, U.S. Pat. No. 4,848,343 to Wallstent and U.S. Pat. No. 5,201,757 to Heyn et al. all of which are incorporated herein in their entirety by reference.

Although all of the above embodiments have bumpers, the use of bumpers is not a necessary feature of the present invention. While all of the above-described embodiments show the use of optional marker bands underneath the proximal and distal ends of the stent, marker bands may be otherwise positioned or need not be used at all.

As depicted, the retractable sheath on the above embodiments is not received interiorly by the catheter. However, the present invention also contemplates a stent-delivery system in which the catheter is constructed and arranged to receive at least part of the retractable sheath interiorly thereof upon retraction of the retractable cover. The present invention also contemplates the use of catheters with full length sheaths such as that described in Imbert, U.S. Pat. No. 4,875,480 and catheters using collapsible sheaths as described in U.S. Pat. No. 5,534,007 and in WO 96/36298 all of which are incorporated in their entirety herein by reference.

The present invention is also directed to a method of securing a stent to a stent delivery system. The method comprises the steps of providing a stent delivery system comprising a catheter with a stent mounting region thereon and a stent holder extending outward from the catheter in the stent mounting region and mounting a stent having one or more retention openings therein on the stent mounting region of the catheter, the stent holder extending into at least one of the retention openings so as to engage the stent. A suitable stent delivery system and stent for the practice of this method has been disclosed above.

The present invention is also directed to a method of securing a stent to a stent delivery system comprising the steps of providing a stent delivery system comprising a catheter with a stent mounting region thereon, the stent mounting region exposed. The system further comprises a retractable sheath having a stent holder extending from the distal end thereof, the retractable sheath retractable between a closed position in which the sheath overlies the stent mounting region of the catheter and an open position in which the sheath does not overly the mounting region. A stent is then mounted on the stent mounting region of the catheter and the retractable sheath moved so that it is in its closed position overlying the stent and stent mounting region of the catheter, the stent holder engaging the stent. A suitable stent delivery system and stent for the practice of this method has been disclosed above.

The present invention is also directed to a method of controllably delivering a self expanding stent to a location in a body lumen using the above-described inventive stent delivery systems. The method uses any of the above-described inventive self-expanding stent delivery systems and comprises the steps of mounting the stent in the unexpanded state on the catheter, covering at least a portion of the stent with a retractable sheath for preventing the stent from self expanding and engaging the stent with the stent holder to prevent the stent from substantially moving in a longitudinal direction. The stent delivery system may optionally be purged of air, such as by flowing a fluid through the delivery system. Finally, the method comprises the additional steps of inserting at least a portion of the stent delivery system (at least the distal portion) into a bodily vessel, delivering the stent to a desired location in the body, fully retracting the retractable sheath thereby allowing the stent to self expand and withdrawing the stent delivery system.

Figure 8:
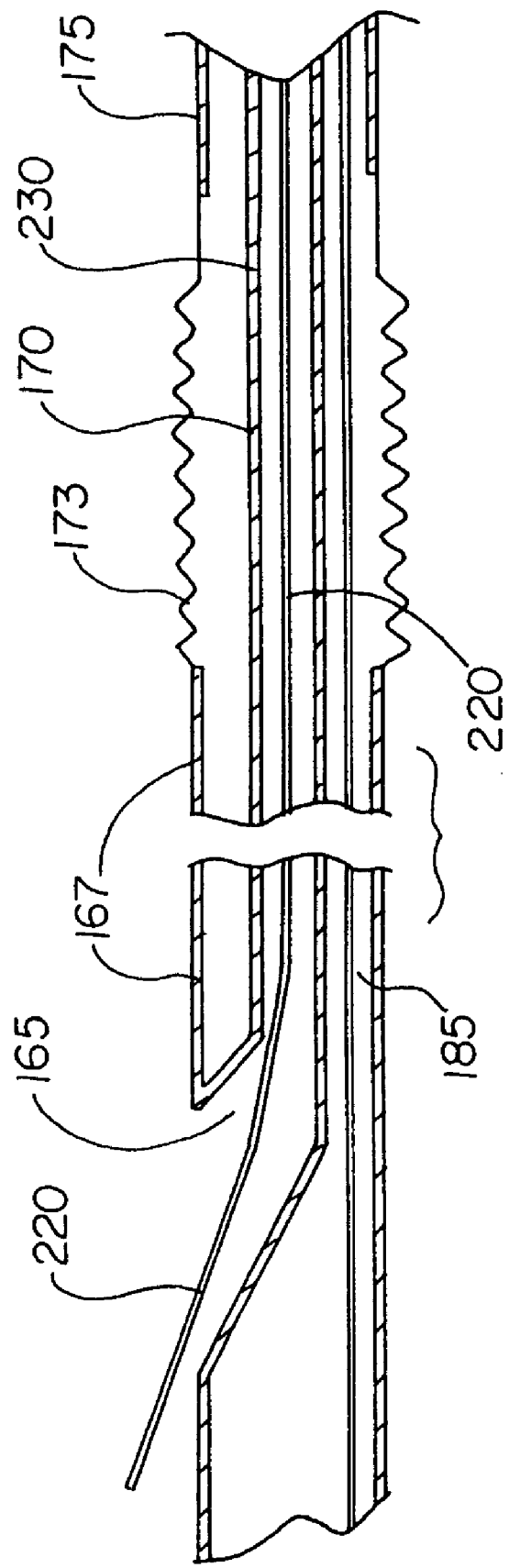
FIG. 8 shows a schematic side view of a portion an inventive stent delivery system configured for rapid-exchange.

While several specific embodiments of the present invention have been described, the invention is directed more generally toward the inclusion of one of the above-described stent holders in any other suitable stent delivery system or catheter design not specifically described herein including over-the-wire and rapid-exchange catheters as well as convertible catheters (catheters that can be used either in an over-the-wire mode or a rapid-exchange mode). In the case of an over-the-wire device, a guidewire may be inserted into the catheter. In the case of a rapid exchange device, as shown in FIG. 8, a guide wire 220 enters the stent delivery device via guide wire inlet 165 distal to the manifold. In the embodiment shown in FIG. 8, guide wire inlet 165 is also proximal to collapsible sheath/shaft 173. Guide wire 220, carried in guide wire lumen 230, extends distally to the distal end of the stent delivery device. A stent may be mounted on guide wire lumen 230 in a manner identical to that disclosed for mounting the stent to the distal end of the catheter in the above embodiments and the stent holder included in the device, as described for the above embodiments. Where typically the usable length of the stent delivery system is approximately 135 cm, for a rapid-exchange catheter the distance from where the guide wire accesses the guide wire lumen to the distal tip will be approximately 5 cm to 45 cm.

A fixed wire version of the inventive stent delivery system may be made by modifying an over-the-wire version of the inventive stent delivery system such that the guide wire is actually fixed to the catheter or another suitable part of the stent delivery system. The fixed wire catheter disclosed in U.S. Pat. No. 5,702,364 to Euteneuer et al. and incorporated herein in its entirety by reference may also be used in conjunction with the present invention to produce a fixed wire stent delivery system. Other suitable designs for fixed wire catheters known in the art may also be applied to the inventive stent delivery system so as produce an inventive fixed wire stent delivery system.

The invention in its various embodiments is further intended for use with other medical treatment devices such as a vena cava filter and a graft, preferably self expanding as well as other suitable self-expanding medical devices.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. A self-expanding stent delivery system comprising:
    a catheter having proximal and distal ends;
    a self-expanding stent concentrically arranged around the catheter near the distal end, the stent having proximal and distal ends, the stent having an unexpanded state and an expanded state following self expansion, the stent having an inner surface which faces the catheter and an outer surface which faces away from the catheter;
    a retractable sheath for covering the stent constructed and arranged for retraction to release the stent to self-expand, the retractable sheath located at the distal end of the catheter and disposed coaxially about the catheter;
    a stent holder adjacent to at least a portion of the stent for holding the stent in place until the retractable sheath is retracted, the stent holder formed of a profiled extrusion around a portion of the catheter, the stent holder frictionally engaging only the inner surface of the proximal end of the stent in the unexpanded state, the stent holder during retraction of the retractable sheath preventing the stent from substantially moving longitudinally until the retractable sheath has been removed from the stent.

2. The stent delivery system of claim 1 further comprising a pull back means for retracting the retractable cover, the pull back means operatively connected to the retractable cover.

3. The stent delivery system of claim 2 wherein the pull back means comprises a pull collar assembly having a pull wire attached thereto, the pull wire extending to the proximal end of the catheter.

4. The stent delivery system of claim 1 further comprising a bumper carried by the catheter and affixed to the catheter at a position adjacent the proximal end of the stent.

5. The stent delivery system of claim 1 further comprising a tip at the distal end of the catheter, the distal end of the sheath abutting the tip to form a stent chamber.

6. The stent delivery system of claim 1 further comprising one or more marker bands carried by the catheter and positioned underneath the stent.

7. The stent delivery system of claim 1 comprising a first marker band underneath the proximal end of the stent and a second marker band underneath the distal end of the stent.

8. The stent delivery system of claim 1 wherein the stent is a nitinol self expanding stent.

9. The stent delivery system of claim 1 further comprising one or more marker bands.

10. The stent delivery system of claim 9 having a first marker band and a second marker band, the first marker band situated at the proximal end of the stent between the stent holder and the catheter.

11. A self-expanding stent delivery system comprising:
    a catheter having proximal and distal ends;
    a self-expanding stent having an unexpanded state and an expanded state, the stent concentrically arranged around the catheter near the distal end, the stent having proximal and distal ends, the stent having an inner surface facing the catheter, the inner surface of the stent in the unexpanded state at a first radial distance from the catheter and an outer surface facing outward, the outer surface of the stent in the unexpanded state at a second radial distance from the catheter, the stent having at least one retention opening therein;
    a retractable sheath for covering the stent constructed and arranged for retraction to release the stent to self-expand, the retractable sheath located at the distal end of the catheter, the retractable sheath having a proximal end and a distal end,
    a stent holder comprising an elastic membrane situated at the distal end of the sheath and arranged so as to frictionally engage at least a portion of the stent during retraction of the retractable sheath and prevent the stent from self deploying.

12. A medical device delivery system comprising:
    a catheter having proximal and distal ends;
    a medical device disposed about the catheter near the distal end, the medical device having an inner surface facing the catheter and an outer surface facing away from the catheter;
    a retractable sheath for covering the medical device, the retractable sheath constructed and arranged for retraction to release the medical device, the retractable sheath located at the distal end of the catheter and disposed coaxially about the catheter, the retractable sheath having a proximal end and a distal end;

a medical device holder adjacent to at least a portion of the medical device for holding the medical device in place until the retractable sheath is retracted, the medical device holder consisting of a profiled extrusion around a portion of the catheter, the medical device holder frictionally engaging only the proximal end of the inner surface of the medical device whereby during retraction of the retractable sheath the medical device holder prevents medical device from substantially moving longitudinally until the retractable sheath has been removed from the medical device.

13. A medical device delivery system comprising:

a catheter having proximal and distal ends;

a medical device concentrically arranged around the catheter near the distal end, the medical device having proximal and distal ends;

a retractable sheath for covering the medical device, the retractable sheath constructed and arranged for retraction to release the medical device, the retractable sheath located at the distal end of the catheter, the retractable sheath having a proximal end and a distal end, a medical device holder located at the distal end of the retractable sheath and comprising a portion of the retractable sheath tapered inward toward the catheter so as to frictionally engage at least a portion of the medical device during retraction of the retractable sheath and prevent the medical device from moving substantially longitudinally whereby during retraction of the retractable sheath the stent holder prevents the stent from substantially moving longitudinally until the retractable sheath has been removed from the stent.

14. A medical device delivery system comprising:

a catheter having proximal and distal ends;

a medical device disposed around the catheter near the distal end, the medical device having proximal and distal ends;

a retractable sheath for covering the medical device constructed and arranged for retraction to release the medical device, the retractable sheath located at the distal end of the catheter, the retractable sheath having a proximal end and a distal end, a medical device holder located at the distal end of the retractable sheath and comprising an elastic membrane situated at the distal end of the sheath and arranged so as to frictionally engage at least a portion of the medical device during retraction of the retractable sheath and prevent the medical device from deploying before the sheath is completely retracted.

15. A method of controllably delivering a self expanding stent having distal and proximal ends, the stent having an unexpanded state and an expanded state, comprising the steps of:

providing a stent delivery system as in claim 1 and a stent;

mounting the stent in the unexpanded state on the catheter;

surrounding at least a portion of the stent with a retractable sheath for preventing the stent from self expanding;

engaging the stent with the stent holder;

inserting at least a portion of the stent delivery system into a bodily vessel;

delivering the stent to a desired location in the body;

fully retracting the retractable sheath thereby allowing the stent to self expand;

deploying the stent; and withdrawing the stent delivery system.

16. The method of claim 15 the retractable sheath having a proximal end and a distal end, the stent holder comprising an elastic membrane situated at the distal end of the sheath and arranged so as to frictionally engage at least a portion of the stent during retraction of the retractable sheath and prevent the stent from self deploying.

17. A method of controllably delivering a self expanding stent having distal and proximal ends, the stent having an unexpanded state and an expanded state, comprising the steps of:

a) providing a self-expanding stent delivery system comprising 1) a catheter having proximal and distal ends;

2) a self-expanding stent concentrically arranged around the catheter near the distal end, the stent having proximal and distal ends, the stent having an unexpanded state and an expanded state following self expansion;

3) a retractable sheath for covering the stent constructed and arranged for retraction to release the stent to self-expand, the retractable sheath located at the distal end of the catheter and disposed coaxially about the catheter;

4) a stent holder adjacent to at least a portion of the stent for holding the stent in place until the retractable sheath is retracted;

whereby during retraction of the retractable sheath the stent holder prevents the stent from substantially moving longitudinally until the retractable sheath has been removed from the stent b) providing a stent;

c) mounting the stent in the unexpanded state on the catheter;

d) surrounding at least a portion of the stent with a retractable sheath for preventing the stent from self expanding;

e) engaging the stent with the stent holder;

f) purging the stent delivery system of air and subsequently inserting at least a portion of the stent delivery system into a bodily vessel;

g) delivering the stent to a desired location in the body;

h) fully retracting the retractable sheath thereby allowing the stent to self expand;

deploying the stent; and i) withdrawing the stent delivery system from the body.

18. A stent delivery system comprising:

a catheter having proximal and distal ends, the catheter having a stent mounting region on the distal end;

a retractable sheath for covering the stent mounting region, the retractable sheath having a proximal end and a distal end, the retractable sheath constructed and arranged for retraction from over the stent mounting region, the retractable sheath located at the distal end of the catheter and disposed coaxially about the catheter;

a stent holder for holding a stent in place until the retractable sheath is retracted, the stent holder located at the distal end of the retractable sheath and comprising a portion of the retractable sheath tapered inward toward the catheter so as to frictionally engage at least a portion of the stent during retraction of the retractable sheath and prevent the stent from moving substantially longitudinally until the retractable sheath has been removed from over a said stent.

19. A method of securing a stent to a stent delivery system comprising the steps of:

providing a stent delivery system comprising a catheter with a stent mounting region thereon, the stent mounting region exposed and a retractable sheath having a stent holder extending from the distal end thereof, the retractable sheath retractable between a closed position in which the sheath overlies the stent mounting region of the catheter and an open position in which the sheath does not overly the mounting region;

mounting a stent on the stent mounting region of the catheter; and moving the retractable sheath so that it is in its closed position overlying the stent and stent mounting region of the catheter, the stent holder engaging the stent.

* * * * *